(12) United States Patent
Yamamura

(10) Patent No.: US 9,635,856 B2
(45) Date of Patent: May 2, 2017

(54) CO-CRYSTAL PRODUCTION METHOD

(71) Applicant: Nippon Soda Co., Ltd., Chiyoda-ku, Tokyo (JP)

(72) Inventor: Satoru Yamamura, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/103,925

(22) PCT Filed: Dec. 10, 2014

(86) PCT No.: PCT/JP2014/082673
§ 371 (c)(1),
(2) Date: Jun. 13, 2016

(87) PCT Pub. No.: WO2015/093367
PCT Pub. Date: Jun. 25, 2015

(65) Prior Publication Data
US 2016/0309718 A1    Oct. 27, 2016

(30) Foreign Application Priority Data

Dec. 19, 2013 (JP) ................................. 2013-262032

(51) Int. Cl.
| | | |
|---|---|---|
| *C07D 249/04* | (2006.01) | |
| *C07D 249/08* | (2006.01) | |
| *C07C 335/12* | (2006.01) | |
| *A01N 43/653* | (2006.01) | |
| *A01N 47/34* | (2006.01) | |

(52) U.S. Cl.
CPC ........... *A01N 43/653* (2013.01); *A01N 47/34* (2013.01); *C07C 335/12* (2013.01); *C07D 249/08* (2013.01)

(58) Field of Classification Search
CPC .... C07C 335/12; C07D 249/04; C07D 249/08
USPC ............ 548/383, 262.2, 268.8; 514/383, 407
See application file for complete search history.

(56) References Cited

U.S. PATENT DOCUMENTS

| | | | |
|---|---|---|---|
| 8,859,607 B2 * | 10/2014 | Israels ................... | A01N 47/34 514/383 |
| 2003/0148887 A1 | 8/2003 | Bratz et al. | |
| 2010/0113543 A1 * | 5/2010 | Israels ................... | A01N 47/34 514/383 |

FOREIGN PATENT DOCUMENTS

| | | |
|---|---|---|
| CN | 101772301 A | 7/2010 |
| JP | 2003-238303 A | 8/2003 |
| JP | 2010-518050 A | 5/2010 |
| JP | 2010-280604 A | 12/2010 |
| JP | 2011-004656 A | 1/2011 |
| JP | 2013-510113 A | 3/2013 |
| WO | WO 2008/096005 A1 | 8/2008 |
| WO | WO 2011/054741 A2 | 5/2011 |

OTHER PUBLICATIONS

International Search Report dated Mar. 3, 2015, in PCT/JP2014/082673.
Office Action dated Mar. 13, 2017, in CN 201480068324.7, with partial English translation of search report.

* cited by examiner

*Primary Examiner* — Venkataraman Balasubramanian
(74) *Attorney, Agent, or Firm* — Foley & Lardner LLP

(57) ABSTRACT

The present invention provides a method for producing a co-crystal including thiophanate-methyl and a triazole-based compound such as tebuconazole and a method for producing an agricultural and horticultural chemical preparation using the co-crystal as a raw material. As one example, the agricultural and horticultural chemical preparation can be obtained by a method including the steps of obtaining a sol including a co-crystal by stirring a suspension including thiophanate-methyl, a triazole compound such as a tebuconazole, a surfactant, a defoaming agent and water at a mixing degree of 0.1-1.0 while holding the temperature of the suspension at 60° C.; and adding auxiliary components such as silica, calcium carbonate and the like to the sol.

7 Claims, 1 Drawing Sheet

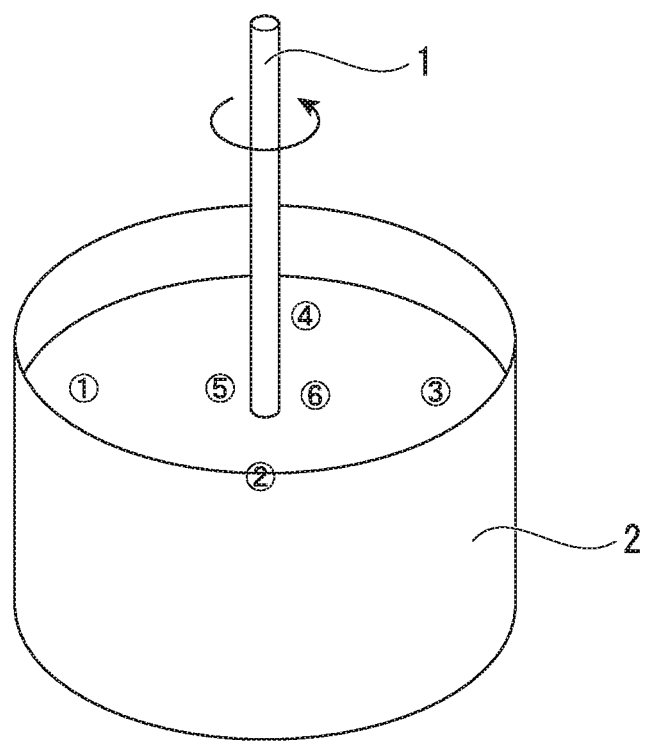

CO-CRYSTAL PRODUCTION METHOD

TECHNICAL FIELD

The present invention relates to a method for producing a co-crystal including thiophanate-methyl and a triazole-based compound, and an agricultural and horticultural chemical composition using the co-crystal as a raw material.

The present application is the U.S. National Stage of PCT/JP2014/082673, filed Dec. 10, 2014, which claims priority on the basis of Japanese Patent Application No. 2013-262032, filed in Japan on Dec. 19, 2013, the contents of which are incorporated herein by reference.

BACKGROUND ART

Thiophanate-methyl and triazole-based compounds such as tebuconazole are known as active ingredients for agricultural and horticultural chemicals. Moreover, thiophanate-methyl is known form a crystalline complex (Patent Document 1). Since the dissolution property or the like changes by the formation of a crystalline complex, that is to say, co-crystal, use of such a co-crystal as a raw material for an agricultural and horticultural chemical composition has been studied.

PRIOR ART DOCUMENTS

Patent Documents

Patent Document 1: Japanese Patent Application Publication No. 2010-518050

DISCLOSURE OF THE INVENTION

Problems to be Solved by the Invention

A co-crystal can be obtained by dispersing thiophanate-methyl and a triazole compound such as tebuconazole in a solvent, followed by stirring the resulting mixture. However, a suspension including thiophanate-methyl and a triazole-based compound such as tebuconazole becomes gelated and solidified if the stirring is stopped, thereby making handling difficult.

The object of the present invention is to provide a method for stably producing a co-crystal in a sol state including thiophanate-methyl and a triazole-based compound such as tebuconazole, and a method for producing an agricultural and horticultural chemical composition using the co-crystal as a raw material.

Means for Solving the Problems

As a result of intensive studies to solve the above problems, the present invention encompassing the following aspects has been completed.

[1] A co-crystal production method including: stirring a suspension including thiophanate-methyl, a triazole-based compound and a liquid medium at a mixing degree of 0.1 to 1.0.
[2] The co-crystal production method according to [1], wherein the triazole-based compound is tebuconazole.
[3] The co-crystal production method according to [1] or [2], wherein the suspension further includes a surfactant.
[4] The co-crystal production method according to any one of [1] to [3], wherein the suspension further includes an anti-foaming agent.
[5] The co-crystal production method according to any one of [1] to [4], wherein the temperature of the suspension during the stirring is 0 to 100° C.
[6] An agricultural and horticultural chemical composition including a co-crystal obtained by the co-crystal production method defined in any one of [1] to [5].
[7] A method for producing an agricultural and horticultural chemical composition including: obtaining a sol including a co-crystal by the co-crystal production method defined in any one of [1] to [5], followed by adding an auxiliary ingredient to the sol.

Effects of the Invention

According to the production method of the present invention, it is possible to stably obtain a co-crystal in a sol state. Since the co-crystal sol obtained by the production method of the present invention is not easily gelated, it is easy to handle, and it is suitable for use as a raw material for an agricultural and horticultural chemical composition.

BRIEF DESCRIPTION OF THE DRAWINGS

FIG. 1 is a diagram showing the sampling points.

BEST MODE FOR CARRYING OUT THE INVENTION

The co-crystal production method according to one embodiment of the present invention includes stirring a suspension including thiophanate-methyl, a triazole-based compound such as tebuconazole, and a liquid medium.

Thiophanate-methyl is a benzimidazole-based fungicidal-active ingredient. Thiophanate-methyl is a compound represented by formula (I).

[Chemical Formula 1]

$$\text{(I)}$$

Thiophanate-methyl used for preparation of the suspension is preferably a powder. The particle size of the thiophanate-methyl powder, namely a particle diameter corresponding to 50% in terms of volume-based cumulative particle size distribution, is preferably 3 to 100 μm.

As the triazole-based compound used in the present invention, cyproconazole, difenoconazole, fenbuconazole, hexaconazole, imibenconazole, ipconazole, metconazole, myclobutanil, propiconazole, simeconazole, tetraconazole, triadimefon or the like may be exemplified, in addition to tebuconazole.

Tebuconazole is a DMI-fungicidal-active ingredient. Tebuconazole is a compound represented by formula (II).

[Chemical Formula 2]

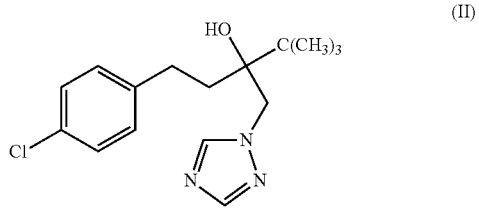

(II)

The triazole-based compound such as tebuconazole used for preparation of the suspension is preferably a powder. The particle size of the triazole-based compound powder such as tebuconazole, namely a particle diameter corresponding to 50% in terms of volume-based cumulative particle size distribution, is preferably 3 to 100 μm.

A molar ratio of thiophanate-methyl/the triazole-based compound such as tebuconazole in the suspension is preferably 1/1 to 3/1.

The total amount of thiophanate-methyl and the triazole-based compound such as tebuconazole in the suspension is generally 10 to 60% by mass, and preferably 20 to 50% by mass.

The liquid medium used in the suspension is not particularly limited as long as it can suspend thiophanate-methyl and the triazole-based compound such as tebuconazole. As the liquid medium, for example, water, monohydric alcohols such as methanol, ethanol, propanol, isopropanol, butanol or the like, glycols such as ethylene glycol, diethylene glycol, propylene glycol, glycerin or the like, or the like may be exemplified. These liquid media can be used singly or used by combining two or more thereof. Among these liquid media, water is preferably used.

The suspension may include an auxiliary ingredient. As the auxiliary ingredient, a surfactant, anti-foaming agent or the like may be exemplified.

As the surfactant, nonionic surfactants such as a polyoxyethylene-added alkyl phenyl ether, a polyoxyethylene-added alkyl ether, a polyoxyethylene-added higher fatty acid ester, a polyoxyethylene-added sorbitan higher fatty acid ester, a polyoxyethylene-added tristyryl phenyl ether or the like, a sulfate ester salt of polyoxyethylene-added alkyl phenyl ether, an alkylbenzene sulfonate, a sulfuric ester salt of a higher alcohol, an alkylnaphthalene sulfonate, a polycarboxylate, a lignin sulfonate, a formaldehyde condensate of an alkyl naphthalene sulfonate, an isobutylene-maleic anhydride copolymer or the like may be exemplified.

The amount of the surfactant in the suspension is preferably 0.1 to 10% by mass, and more preferably 1 to 5% by mass.

As the anti-foaming agent, a silicone-based anti-foaming agent, an organic anti-foaming agent or the like may be exemplified. Among the examples, a silicone-based anti-foaming agent is preferable. As the silicone-based anti-foaming agent, an oil type, oil compound type, solution type, emulsion type, self-emulsifying type or the like may be used. The amount of the anti-foaming agent in the suspension is preferably 0.01 to 1% by mass, and more preferably 0.1 to 0.5% by mass.

The suspension is not particularly limited in terms of the preparation method. For example, the suspension can be obtained by adding thiophanate-methyl powder, the triazole-based compound powder such as tebuconazole and the auxiliary component all together or sequentially to the liquid medium; or by adding the auxiliary component such as a surfactant, an anti-foaming agent or the like to the liquid medium in advance, followed by adding thiophanate-methyl powder and the triazole-based compound powder such as tebuconazole. At the suspension stage, it is not necessary that each component be homogeneously dispersed, and it is acceptable for some of the components to be precipitated.

The prepared suspension is stirred under a condition of a mixing degree of 0.1 to 1.0, and preferably 0.17 to 1.0. The mixing degree is a value defined by a ratio ($\sigma_r/\sigma_{1\ min}$) of a standard deviation $\sigma_r$ of a concentration of a liquid collected after stirring the suspension to a completely mixed state to the standard deviation $\sigma_{1\ min}$ of a concentration of a liquid collected after stirring the suspension for 1 min. The higher mixing degree represents the stronger stirring force.

The mixing degree in a batch-type mixer is determined in the following manner. 12 g of xanthan gum (Kelzan S, manufactured by CP Kelco Co., Ltd.) and 988 g of water are mixed to prepare a 1.2% xanthan gum solution (viscosity of about 1,500 mPa·s). 10 g of a suspension agent (Topsin-M sol, manufactured by Nippon Soda Co., Ltd.) containing 40% of thiophanate-methyl is added to the 1.2% xanthan gum gel solution, followed by stirring for 1 minute. Sample liquids are collected from the six points shown in FIG. 1 after stopping the stirring. Concretely, the six points are four points which are made by circumferentially dividing the vicinity of the vessel wall into four equal parts and two points which are diagonal to each other in the vicinity of the stirring blade axis. The collecting is conducted at a depth of about 50 mm from a static liquid surface. The standard deviation of the concentration of thiophanate-methyl of these collected sample liquids was set to $\sigma_{1\ min}$.

After the sample liquid is collected, stirring using an anchor blade at 200 rpm and Physcotron at 5,000 rpm are performed at the same time for 15 min. The stirring is stopped and the liquid is collected from the six points shown in FIG. 1. Concretely, the six points are four points which are made by circumferentially dividing the vicinity of the vessel wall into four equal parts and two points which are diagonal to each other in the vicinity of the stirring blade axial. Collecting is conducted at a depth of about 50 mm from a static liquid surface. The standard deviation of the concentration of thiophanate-methyl of these collected sample liquids was set to $\sigma_r$.

The mixing degree in the continuous mixer is determined in the following manner. The liquid is extracted randomly or at regular intervals when the average residence time is 1 minute and the standard deviation of the concentration of thiophanate-methyl in the collected liquid is set to σ 1 min. When collecting the liquid at the point where the average residence time is 1 minute is difficult, it is possible to determine the value by extrapolating or interpolating from the value of the standard deviation of the concentration of thiophanate-methyl in the liquid withdrawn from a point where the average residence time is less than 1 minute, or the point where the average residence time exceeds 1 minute. The completely mixed state is realized in the same manner as the case of a batch mixer, and the standard deviation $\sigma_r$ is determined.

The mixing degree can be adjusted by the shape and size of the stirring blade, the shape and size of the container, and the rotational speed of the stirring blade. As the blade shape, a paddle blade, flat paddle blade, anchor blade, turbine blade, ribbon blade, screw blade, propeller blade, gate blade, spool blade or the like may be exemplified.

Although temperature of the suspension at the time of stirring is not particularly limited, it is usually 0 to 100° C., preferably 5 to 75° C., and more preferably 15 to 65° C.

Although the stirring time is not particularly limited, it may be determined by monitoring the change of the solid particles in the suspension.

It can be considered that the co-crystal of the present invention is formed and stabilized by actions such as hydrogen bonding between the molecules, it orbitals stacking, van der Waals forces or the like.

Formation of the co-crystal according to the present invention can be confirmed by thermal analysis (TG/DTA), infrared absorption spectrum (IR), X-ray diffraction pattern, 13C-CP/MAS-solid state NMR spectrum, or the like. In addition, the composition of the co-crystal can be confirmed by thermal analysis, differential scanning calorimetry (DSC), 1H-NMR spectrum, 13C-NMR spectrum, 29Si-NMR spectrum, gel filtration chromatography (GPC), high-performance liquid chromatography (HPLC), elemental analysis, or the like.

The co-crystal manufactured in this manner can be used as is or can be used by isolating and purifying to manufacture the agricultural and horticultural chemical composition according to need.

The agricultural and horticultural chemical composition of the present invention contains the co-crystal according to the present invention. The agricultural and horticultural chemical composition of the present invention may contain other agricultural and horticultural chemical active ingredients in addition to the co-crystal, or may contain auxiliary ingredients, depending on the application and dosage form.

As the dosage form of the agricultural and horticultural chemical composition of the present invention, for example, powder formulation, wettable powder, water-dispersible granule, granule, suspension, tablet, seed coating agent, flowable agent, suspo-emulsion or the like may be exemplified.

As the auxiliary ingredient which may be contained in the agricultural and horticultural chemical composition of the present invention, surfactant, bulking agent, effect-enhancing aid, antioxidant, ultraviolet absorber, stabilizing agent or the like may be exemplified.

As the surfactant which may be included in the agricultural and horticultural chemical composition of the present invention, for example, nonionic surfactants such as a polyoxyethylene-added alkyl phenyl ether, a polyoxyethylene-added alkyl ether, a polyoxyethylene-added higher fatty acid ester, a polyoxyethylene-added sorbitan higher fatty acid ester, a polyoxyethylene-added tristyryl phenyl ether or the like, a sulfate ester salt of polyoxyethylene-added alkyl phenyl ether, an alkyl benzene sulfonate, a sulfate ester salt of a higher alcohol, an alkylnaphthalene sulfonate, a polycarboxylate, a lignin sulfonate, a formaldehyde condensate of alkyl naphthalene sulfonate, an isobutylene-maleic anhydride copolymer or the like may be exemplified.

As the bulking agent that may be contained in the agricultural and horticultural chemical composition of the present invention, for example, a solvent such as water, glycerin, ethylene glycol, propylene glycol, dimethyl sulfoxide, dimethylacetamide, N-methylpyrrolidone, γ-butyrolactone, alcohol, aliphatic hydrocarbon, aromatic hydrocarbon; a thickener, stabilizer, binder such as polyvinylpyrrolidone, polyvinyl alcohol, polyvinyl acetate, polyethylene glycol, carboxymethyl cellulose, hydroxypropyl cellulose, gum arabic, xanthan gum, gelatin, casein, pectin, sodium alginate; a solid carriers, for example, a mineral powder such as talc, clay, bentonite, kaolinite clay, montmorillonite, pyrophyllite, acid clay, diatomaceous earth, vermiculite, apatite, gypsum, mica, silica sand, calcium carbonate, light stone powder or the like; synthetics such as white carbon (amorphous silica), titanium dioxide; vegetable powders such as crystalline cellulose, starch, wood flour, cork, coffee grounds or the like; polymer compounds such as polyvinyl chloride, petroleum resin; water-soluble component such as ammonium sulfate, ammonium nitrate, ammonium chloride, potassium phosphate, potassium chloride, urea, sugars or the like; or the like may be exemplified.

The agricultural and horticultural chemical composition of the present invention may contain other agricultural and horticultural chemical active ingredients in addition to the co-crystal. Other agricultural and horticultural chemical active ingredients that may be contained in the agricultural and horticultural chemical composition of the present invention are not particularly limited. For example, insecticides, miticides, nematicides, fungicides, herbicides, plant growth regulators, resistance-inducing agents, pest repellents, antiviral agents or the like may be exemplified. More specifically, the following components are exemplified.

Insecticides/acaricides, nematocides, soil pesticides, and anthelmintics:

(1) Organic (thio)phosphate-based: acephate, azamethiphos, azinphos-methyl, azinphos-ethyl, bromophos-ethyl, bromfenvinphos, BRP, chlorpyrifos, chlorpyrifos-methyl, chlorpyrifos-ethyl, chlorfenvinphos, cadusafos, carbophenothion, chloroethoxyphos, chloromephos, coumaphos, cyanofenphos, cyanophos, CYAP, dichlorvos, dicrotophos, dimethoate, disulfoton, demeton-S-methyl, dimethylvinphos, demeton-S-methylsulfone, dialiphos, diazinon, diclofenthion, dioxabenzophos, ethion, ethoprophos, etrimfos, EPN, fenamiphos, fenitrothion, fenthion, fensulfothion, flupyrazophos, fonofos, fonofos, formothion, phosmethylan, heptenophos, isazophos, iodinefenphos, isofenphos, isoxathion, iprobenfos, malathion, mevinphos, methamidophos, methidathion, monocrotophos, mecarbam, metacriphos, naled, omethoate, oxydemeton-methyl, paraoxon, parathion, parathion methyl, phenthoate, phosalone, phosmet, phosphamidon, phorate, phoxim, pirimiphos-methyl, pirimiphos-ethyl, profenofos, prothiofos, fosthiazate, phosphocarb, propaphos, propetamphos, prothoate, pyridaphenthion, pyraclofos, quinalphos, salithion, sulprophos, sulfotep, tetrachlorvinphos, terbufos, triazophos, trichlorfon, tebupirimfos, temephos, thiometon, and vamidothion;

(2) Carbamate-based: alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, furathiocarb, XMC, aldoxycarb, allyxycarb, aminocarb, bufencarb, butacarb, butocarboxim, butoxycarboxim, cloethocarb, dimetilan, formetanate, isoprocarb, metam-sodium, metolcarb, promecarb, thiofanox, trimethacarb, and xylycarb;

(3) Pyrethroid-based: allethrin, bifenthrin, cyfluthrin, beta-cyfluthrin, cyhalothrin, lambda-cyhalothrin, cyphenothrin, cypermethrin, alpha-cypermethrin, beta-cypermethrin, zeta-cypermethrin, delta-methrin, esfenvalerate, etofenprox, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, transpermethim, empenthrin, fenfluthrin, fenpirithrin, flubrocythrinate, flufenoprox, flumethrin, metofluthrin, phenothrin, protrifenbute, pyresmethrin, and terallethrin;

(4) Growth regulators:

(a) Chitin synthesis inhibitors: chlorfluazuron, diflubenzuron, flucycloxuron, flufenoxuron, hexaflumuron, lufenuron, novaluron, teflubenzuron, triflumuron, bistrifluron, noviflumuron, buprofezin, hexythiazox, etoxazole, clofentezine, fluazuron, and penfluron;
(b) Ecdysone antagonists: halofenozide, methoxyfenozide, tebufenozide, chromafenozide, and azadirachtin;
(c) Juvenile hormone-like substances: pyriproxyfen, methoprene, diofenolan, epofenonane, hydroprene, kinoprene, and triprene; and
(d) Lipid biosynthesis inhibitors: spirodiclofen, spiromesifen, and spirotetramat;
(5) Nicotine receptor agonist/antagonist compounds: nicotine, bensultap, and cartap;
(6) GABA antagonist compounds:
(a) acetoprole, ethiprole, fipronil, vaniliprole, pyrafluprole, pyriprole; and
(b) Organochlorine-based: camphechlore, chlordane, endosulfan, HCH, γ-HCH, heptachlor, and methoxychlor;
(7) Macrocyclic lactone insecticides: abamectin, emamectin benzoate, milbemectin, lepimectin, spinosad, ivermectin, seramectin, doramectin, epinomectin, moxidectin, milbemycin, and milbemycin oxime;
(8) METI I compounds: fenazaquin, pyridaben, tebufenpyrad, tolfenpyrad, flufenerim, hydramethylnon, fenpyroxymate, pyrimidifen, and dicofol;
(9) METI II and III compounds: acequinocyl, fluacrypyrim, and rotenone;
(10) Uncoupling agent compounds: chlorfenapyr, binapacryl, dinobuton, dinocap, and DNOC;
(11) Oxidative phosphorylation inhibitor compounds: cyhexatin, diafenthiuron, fenbutatin oxide, propargite, and azocyclotin;
(12) Molting disruption compounds: cyromazine;
(13) Mixed function oxidase inhibitor compounds: piperonyl butoxide;
(14) Sodium channel blocker compounds: indoxacarb and metatlumizone;
(15) Microbial agricultural and horticultural chemicals: BT agents, insect pathogen viral agents, insect pathogen fungal agents, nematode pathogen fungal agents; bacillus, beauveria bassiana, metarhizium anisopliae, paecilomyces, thuringiensin, and verticillium;
(16) Latrophilin receptor agonists: depsipeptide, cyclodepsipeptide, 24-membered cyclodepsipeptide, and emodepside;
(17) Octopamine agonists: amitraz;
(18) Ryanodine receptor agonists: flubendiamide, and chlorantraniliprole;
(19) Magnesium-stimulated ATPase inhibitors: thiocyclam, thiosultap, and nereistoxin;
(20) Feeding inhibitors: pymetrozine;
(21) Acari growth inhibitors: clofentezine and etoxazole;
(22) Other compounds (substances): benclothiaz, bifenazate, pyridalyl, sulfur, cyenopyrafen, cyflumetofen, amidoflumet, tetradifon, chlordimeform, 1,3-dichloropropene, DCIP, phenisobromolate, benzomate, methaldehyde, spinetoram, pyrifluquinazon, benzoxymate, bromopropylate, quinomethionate, chlorobenzilate, chloropicrin, chlothiazoben, dicyclanil, fenoxacrim, fentrifanil, flubenzimine, fluphenzine, gossyplure, japonilure, metoxadiazone, petroleum, potassium oleate, sulfluramid, tetrasul, and triarathene; afidopyropen, pyflubumide, flometoquin, flufiprole, fluensulfone, meperfluthrin, tetramethylfluthrin, imicyafos, tralopyril, diflovidazin, dimefluthrin, and methylneodecanamide;
(23) Anthelmintics:
(a) Benzimidazole-based: fenbendazole, albendazole, triclabendazole, and oxybendazole;
(b) Salicylanilide-based: closantel and oxyclozanide;
(c) Substituted phenol-based: nitroxinil;
(d) Pyrimidine-based: pyrantel;
(e) Imidazothiazole-based: levamisole;
(f) Tetrahydropyrimidine: praziquantel; and
(g) other anthelmintic drugs: cyclodiene, ryania, clorsulon, metronidazole, and demiditraz;
Fungicides:
(1) Benzimidazole-based: benomyl, carbendazim, fuberidazole, thiabendazole, and chlorfenazole;
(2) Dicarboxyimide-based: chlozolinate, iprodione, procymidone, and vinclozolin;
(3) DMI-fungicide-based: imazalil, oxpoconazole, pefurazoate, prochloraz, triflumizole, triforine, pyrifenox, fenarimol, nuarimol, azaconazole, bitertanol, bromuconazole, cyproconazole, difenoconazole, diniconazole, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tetraconazole, triadimefon, triadimenol, triticonazole, etaconazole, furconazole-cis, diclobutrazol, diniconazole M, dodemorph acetate, fluconazole, imazalil-sulfate, naftifine, uniconazole P, viniconazole, and voriconazole;
(4) Phenylamide-based: benalaxyl, benalaxyl-M, clozylacon, furalaxyl, metalaxyl, metalaxyl M, oxadixyl, and ofurace;
(5) Amine-based: aldimorph, dodemorph, fenpropimorph, tridemorph, fenpropidin, piperalin, and spiroxamine;
(6) Phosphorothiolate-based: EDDP, iprobenfos, and pyrazophos;
(7) Dithiolane-based: isoprothiolane;
(8) Carboxamide-based: benodanil, boscalid, carboxin, fenfuran, flutolanil, furametpyr, mepronil, oxycarboxin, penthiopyrad, thifluzamide, bixafen, isopyrazam, penflufen, fluxapyroxad, and sedaxane;
(9) Hydroxy(2-amino)pyrimidine-based: bupirimate, dimethirimol, and ethirimol;
(10) AP fungicides (anilinopyrimidine)-based: cyprodinil, mepanipyrim, pyrimethanil, and andoprim;
(11) N-phenylcarbamate-based: diethofencarb;
(12) QoI fungicides (Qo inhibitors)-based: azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen, ametoctradin, pyrametostrobin, pyraoxystrobin, pyribencarb, coumethoxystrobin, coumoxystrobin, enestrobin, phenoxystrobin, and triclopyricarb;
(13) PP fungicides (phenylpyrrole)-based: fenpiconil, and fludioxonil;
(14) Quinoline-based: quinoxyfen;
(15) AH fungicedes (aromatic hydrocarbon)-based: biphenyl, chloroneb, dichloran, quintozene, and tecnazene;
(16) MBI-R-based: fthalide, pyroquilon, and tricyclazole;
(17) MBI-D-based: carpropamid, diclocymet, and fenoxanil;
(18) SBI agents: fenhexamid, pyributicarb, and terbinafine;
(19) Phenylureas: pencycuron;
(20) QiI fungicides (Qi inhibitors): cyazofamid, amisulbrom, and furmecyclox;
(21) Benzamide-based: zoxamide;
(22) Enopyranurone-based: blasticidin, and mildiomycin;
(23) Hexopyranosyl-based: kasugamycin, and kasugamycin hydrochloride;
(24) Glucopyranosyl-based: streptomycin, validamycin, and validamycin A;
(25) Cyanoacetoamide-based: cymoxanil;
(26) Carbamate-based: iodocarb, propamocarb, prothiocarb, and polycarbamate;

(27) Uncoupling agents: binapacryl, dinocap, ferimzone, fluazinam, and meptyldinocap;
(28) Organic tin compounds: triphenyltin acetate, triphenyltin chloride, and triphenyltin hydroxide;
(29) Phosphate esters: phosphorous acid, tolclofos-methyl, fosetyl, and tolclofos-methyl;
(30) Phthalamidic acid-based: tecloftalam;
(31) Benzotriazine-based: triazoxide;
(32) Benzene sulfonamide-based: flusulfamide;
(33) Pyridazinones: diclomezine;
(34) CAA fungicides (carbonic acid amide)-based: dimethomorph, flumorph, benthiavalicarb-isopropyl, iprovalicarb, mandipropamide, and valifenalate;
(35) Tetracyclines: oxytetracycline;
(36) Thiocarbamate-based: methasulfocarb;
(37) Resistance inducer: acibenzolar S-methyl, probenazole, tiadinil, and isotianil;
(38) Other compounds: etridiazole, polyoxin, polyoxorim, oxolinic acid, hydroxyl-isoxazole, octhilinone, silthiofam, diflumetorim, ethaboxam, cyflufenamid, proquinazid, metrafenone, fluopicolide, Bordeaux mixture, copper naphthalate, copper oxide, copper oxychloride sulfate, copper sulfate, mancopper, bis(8-quinolinolato)copper(II), cupric hydroxide, organic copper, sulfur, calcium polysulfide, ferbam, manzeb, maneb, metiram, propineb, thiuram, zineb, ziram, captan, captafol, folpet, chlorothalonil, dichlofluanid, tolyltluanid, dodine, guazatine, iminoctadine, iminoctadine acetate, iminoctadine alkylbenzene sulfonate, anilazine, dithianon, chloropicrin, dazomet, chinomethionat, cyprofuram, agrobacterium, fluoroimide, isofetamid, tolprocarb, fenpyrazamine, pyriofenone, tebufloquin, fluopyram, zarilamid, fluorofolpet, propamidine, edifenphos, benthiazole, bethoxazin, capsaicin, carvone, cufraneb, mancozeb, cyprosulfamide, debacarb, dichlorophen, difenzoquat, difenzoquat-methyl sulfonate, diphenylamine, flumetover, fluoroimide, flutianil, fosetyl-aluminum, fosetyl-calcium, fosetyl-sodium, irumamycin, methyl isothiocyanate (MITC), natamycin, nitro-tar-isopropyl, oxamocarb, oxyfenthiin, propamocarb-fosetylate, propamocin-sodium, pyrimorph, pyrrolnitrin, tolnifanide, and trichlamide;

Plant Growth Regulators:

abscisic acid, indole butyric acid, uniconazole, ethychlozate, ethephon, cloxyfonac, chlormequat, a chlorella extract, calcium peroxide, cyanamide, dichlorprop, gibberellin, daminozide, decyl alcohol, trinexapac-ethyl, mepiquat-chloride, paclobutrazol, paraffin wax, piperonyl butoxide, pyraflufen-ethyl, flurprimidol, prohydrojasmon, a prohexadione-calcium salt, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene, and aviglycine hydrochloride.

The production method of the agricultural and horticultural chemical composition of the present invention is not particularly limited. For example, a method including mixing the co-crystal of the present invention in the obtained form (for example, sol state) with other agricultural and horticultural chemical components, if necessary, auxiliary ingredients, and formulating it; a method including isolating the co-crystal of the present invention, mixing the isolated co-crystal with auxiliary ingredients, and formulating it; are exemplified.

The application method of the agricultural and horticultural chemical composition according to the present invention is not particularly limited. For example, spraying on foliage; spraying on propagation materials such as seeds, seed potatoes, bulbs; treatments such as dressing, spraying, dipping; tree trunk injection; treatments such as spraying on the surface of soil or a cultivation carrier, mixing with or irrigation to the soil or cultivation carrier, planting hole treatment; paddy surface application, and the like, may be exemplified. The co-crystal obtained by the method of the present invention can be used, in addition to agricultural and horticultural purposes, as a termiticide, sanitary pest control agent, wood pest control agent, and the like.

EXAMPLES

The following provides a more detailed explanation of the present invention by way of Examples. However, the present invention is not limited to the following Examples.

The physical properties of the Examples were determined by the following method.

(Mixing Degree)

The mixing degree in a batch-type mixer was determined in the following manner. 12 g of xanthan gum (Kelzan S, manufactured by CP Kelco Co., Ltd.) and 988 g of water were mixed to prepare a 1.2% xanthan gum solution (viscosity of about 1,500 mPa·s). 10 g of a suspension agent (Topsin-M sol, manufactured by Nippon Soda Co., Ltd.) containing 40% of thiophanate-methyl was added to the 1.2% xanthan gum gel solution, followed by stirring for 1 minute. Sample liquids were collected from the six points shown in FIG. 1 after stopping the stirring. Concretely, the six points were four points which were made by circumferentially dividing the vicinity of the vessel wall into four equal parts and two points which were diagonal to each other in the vicinity of the stirring blade axial. The collecting was conducted at a depth of about 50 mm from a static liquid surface. The standard deviation of the concentration of the collected sample liquids was set to $\sigma_{1\ min}$.

After the sample liquid was collected, stirring using an anchor blade at 200 rpm and Physcotron at 5,000 rpm was performed simultaneously for 15 min. The liquid was collected from the six points shown in FIG. 1 after stopping the stirring. Concretely, the six points were four points which were made by circumferentially dividing the vicinity of the vessel wall into four equal parts and two points which were diagonal to each other in the vicinity of the stirring blade axial. Collecting was conducted at a depth of about 50 mm from a static liquid surface. The standard deviation of the concentration of the collected sample liquids was set to $\sigma_r$. The mixing degree $M_{1\ min}$ was calculated according to the formula: $\sigma_r/\sigma_{1\ min}$.

The mixing degree in various stirring devices, stirring blades, containers and rotational speeds are shown in Table 1.

TABLE 1

| Device | Stirring device | Stirring blade | Rotational speed (rpm) | Container | Mixing degree $M_{1\ min}$ |
|---|---|---|---|---|---|
| A | Three-one motor (manufactured by AS ONE Co., Ltd.) | Anchor paddle (blade diameter 110 mmφ) | 200 | 2 L capacity SUS cup (φ138 mm × 147 mm) | 0.256 |

TABLE 1-continued

| Device | Stirring device | Stirring blade | Rotational speed (rpm) | Container | Mixing degree $M_{1\ min}$ |
|---|---|---|---|---|---|
| B | Labolution (manufactured by PRIMIX Corporation) | Homo Disper TK-2.5 (blade diameter 40 mmφ) | 5000 | 2 L capacity SUS cup (φ138 mm × 147 mm) | 0.174 |
| C | Labolution (manufactured by PRIMIX Corporation) | Homo Mixer MARK II | 5000 | 2 L capacity SUS cup (φ138 mm × 147 mm) | 0.206 |
| D | Three-one motor (manufactured by AS ONE Co., Ltd.) | Fan turbine (blade diameter 75 mmφ) | 300 | 2 L capacity SUS cup (φ138 mm × 147 mm) | 0.009 |
| E | Three-one motor (manufactured by AS ONE Co., Ltd.) | Anchor paddle (blade diameter 110 mmφ) | 200 | 10 L capacity SUS cup (φ250 mm × 222 mm) | 0.083 |
| F | Three-one motor (manufactured by AS ONE Co., Ltd.) Physcotron NS-52 (manufactured by Microtec. Co., Ltd) | Fan turbine (blade diameter 75 mmφ) Shield-type generater shaft (diameter 20 mmφ) | 300 5000 | 2 L capacity SUS cup (φ138 mm × 147 mm) | 0.012 |
| G | Three-one motor (manufactured by AS ONE Co., Ltd.) | Fan turbine (blade diameter 75 mmφ × 2) | 300 | 2 L capacity SUS cup (φ138 mm × 147 mm) | 0.011 |

(Flowability)

30 g of the sample liquid was charged to a beaker (weight W0) of 100 ml capacity. The weight (W1) including the tare was measured. The sample liquid was drained by tilting the beaker at 45 degrees and holding for 120 seconds. Then the weight (W2) of the beaker with 100 ml capacity was measured. The flowability F (%) was calculated according to the formula: (W1−W2)/(W1−W0)×100.

W0=Weight of the beaker with 100 ml capacity (g)
W1=Total weight of the beaker with 100 ml capacity and the liquid before draining (g)
W2=Total weight of the beaker with 100 ml capacity and the remained liquid (g)

The flowability before the temperature rise (initial flowability) and the flowability 20 minutes after the temperature rise (flowability after 20 minutes) were measured. If the flowability after 20 minutes was 90% or more, the handling ability of the liquid was deemed good.

Example 1

360.0 g of thiophanate-methyl, 105.0 g of tebuconazole, 25.0 g of PO-EO block polymer (Pluronic PE10500; manufactured by BASF), 6.0 g of silicone-based anti-foaming agent (SILFORM SE-39; manufactured by Asahi Kasei Wacker Silicone Co., Ltd.), and 311.0 g of water were weighed in a SUS-made cup (outer size φ138 mm×147 mm/manufactured by AS ONE Co., Ltd.) of 2 L capacity and stirred at 200 rpm by using a three-one motor (solid concentration 57.6%). An anchor paddle (blade diameter 110 mmφ, shaft 8 mm×500 mm/manufactured by Shinko Seisakusho Co., Ltd.) was used as the stirring blade. The mixing degree of device A was 0.256. While stirring the liquid, the temperature was raised until the liquid temperature reached 60° C. Then the liquid was stirred for about 20 minutes while maintaining the liquid temperature at 60° C. In this way, a liquid including the co-crystal of thiophanate-methyl and tebuconazole was obtained. The flowability of the liquid is shown in Table 2.

Examples 2-5

The liquids including the co-crystal of thiophanate-methyl and tebuconazole were obtained in the same manner as in Example 1 except for changing the formulation thereof to the formulations shown in Table 2. The flowabilities of the liquids are shown in Table 2.

Example 6

360.0 g of thiophanate-methyl, 105.0 g of tebuconazole, 25.0 g of PO-EO block polymer (Pluronic PE10500; manufactured by BASF), 10.0 g of anionic surfactant (Tamol DN; manufactured by BASF), 6.0 g of silicone-based anti-foaming agent (SILFORM SE-39; manufactured by Asahi Kasei Wacker Silicone Co., Ltd.), and 311.0 g of water were weighed and put in a SUS-made cup (outer size φ138 mm×147 mm/manufactured by AS ONE Co., Ltd.) with 2 L capacity, followed by stirring at 200 rpm using a three-one motor (solid concentration 57.6%). An anchor paddle (blade diameter 110 mmφ, shaft 8 mm×500 mm/manufactured by Shinko Seisakusho Co., Ltd.) was used as the stirring blade. The mixing degree of this device A was 0.256. While stirring the liquid, the temperature was raised until the liquid temperature reached 60° C. Then the liquid was stirred for about 20 minutes while maintaining the liquid temperature at 60° C. In this way, a liquid including the co-crystal of thiophanate-methyl and tebuconazole was obtained. The flowability of the liquid is shown in Table 2.

Example 7

The liquid including the co-crystal of thiophanate-methyl and tebuconazole was obtained in the same manner as in Example 6 except for changing the formulation thereof to the formulations shown in Table 2. The flow properties of the liquids are shown in Table 2.

Example 8

The liquid including the co-crystal of thiophanate-methyl and tebuconazole was obtained in the same manner as in Example 6 except for changing device A to device B (mixing degree of 0.174). The flowability of the liquid is shown in Table 2.

Example 9

The liquid including the co-crystal of thiophanate-methyl and tebuconazole was obtained in the same manner as in Example 6 except for changing device A to device C (mixing degree of 0.206). The flowability of the liquid is shown in Table 2.

TABLE 2

| | Example | | | | | | | | |
|---|---|---|---|---|---|---|---|---|---|
| | 1 | 2 | 3 | 4 | 5 | 6 | 7 | 8 | 9 |
| Thiophanate-methyl [g] | 360.0 | 105.0 | 108.0 | 52.5 | 31.5 | 360.0 | 31.5 | 360.0 | 360.0 |
| Tebuconazole [g] | 105.0 | 105.0 | 31.5 | 52.5 | 31.5 | 105.0 | 31.5 | 105.0 | 105.0 |
| Pluronic PE10500 [g] | 25.0 | 25.0 | 25.0 | 25.0 | 25.0 | 25.0 | 25.0 | 25.0 | 25.0 |
| Tamol DN [g] | 0.0 | 0.0 | 0.0 | 0.0 | 0.0 | 10.0 | 10.0 | 10.0 | 10.0 |
| SILFORMSE-39 [g] | 6.0 | 6.0 | 6.0 | 6.0 | 6.0 | 6.0 | 6.0 | 6.0 | 6.0 |
| Water [g] | 311.0 | 433.0 | 357.0 | 378.0 | 359.0 | 311.0 | 359.0 | 311.0 | 311.0 |
| Solid concentration [%] | 57.6 | 31.2 | 26.4 | 20.4 | 13.9 | 56.9 | 13.6 | 56.9 | 56.9 |
| Device | A | A | A | A | A | A | A | B | C |
| Mixing degree $M_{1\,min}$ | 0.256 | 0.256 | 0.256 | 0.256 | 0.256 | 0.256 | 0.256 | 0.174 | 0.206 |
| Initial flowability [%] | 98.1 | 99.0 | 99.1 | 99.5 | 99.3 | 99.3 | 99.1 | 99.0 | 99.1 |
| Flowability after 20 minutes | 96.8 | 97.9 | 97.4 | 98.5 | 97.8 | 96.4 | 96.9 | 97.1 | 96.3 |

Comparative Examples 1-5

The liquids including the co-crystal of thiophanate-methyl and tebuconazole were obtained in the same manner as in Examples 1-5 except for changing device A to device D (mixing degree of 0.009). The flow properties of the liquid are shown in Table 3.

Comparative Example 6

The liquid including the co-crystal of thiophanate-methyl and tebuconazole was obtained in the same manner as in Example 6 except for changing device A to device D (mixing degree of 0.009). The flowability of the liquid is shown in Table 3.

Comparative Example 7

The liquid including the co-crystal of thiophanate-methyl and tebuconazole was obtained in the same manner as in Example 1 except for changing device A to device E (mixing degree of 0.083). The flowability of the liquid is shown in Table 3.

Comparative Example 8

The liquid including the co-crystal of thiophanate-methyl and tebuconazole was obtained in the same manner as in Example 1 except for changing device A to device F (mixing degree of 0.012). The flowability of the liquid is shown in Table 3.

Comparative Example 9

The liquid including the co-crystal of thiophanate-methyl and tebuconazole was obtained in the same manner as in Example 1 except for changing device A to device G (mixing degree of 0.011). The flowability of the liquid is shown in Table 3.

TABLE 3

| | Comparative Example | | | | | | | | |
|---|---|---|---|---|---|---|---|---|---|
| | 1 | 2 | 3 | 4 | 5 | 6 | 7 | 8 | 9 |
| Thiophanate-methyl [g] | 360.0 | 105.0 | 108.0 | 52.5 | 31.5 | 360.0 | 360.0 | 360.0 | 360.0 |
| Tebuconazole [g] | 105.0 | 105.0 | 31.5 | 52.5 | 31.5 | 105.0 | 105.0 | 105.0 | 105.0 |
| Pluronic PE10500 [g] | 25.0 | 25.0 | 25.0 | 25.0 | 25.0 | 25.0 | 25.0 | 25.0 | 25.0 |
| Tamol DN [g] | 0.0 | 0.0 | 0.0 | 0.0 | 0.0 | 10.0 | 0.0 | 0.0 | 0.0 |
| SILFORMSE-39 [g] | 6.0 | 6.0 | 6.0 | 6.0 | 6.0 | 6.0 | 6.0 | 6.0 | 6.0 |
| Water [g] | 311.0 | 433.0 | 357.0 | 378.0 | 359.0 | 311.0 | 311.0 | 311.0 | 311.0 |
| Solid concentration [%] | 57.6 | 31.2 | 26.4 | 20.4 | 13.9 | 56.9 | 57.6 | 57.6 | 57.6 |
| Device | D | D | D | D | D | D | E | F | G |
| Mixing degree $M_{1\,min}$ | 0.009 | 0.009 | 0.009 | 0.009 | 0.009 | 0.009 | 0.083 | 0.012 | 0.011 |

TABLE 3-continued

| | Comparative Example | | | | | | | | |
|---|---|---|---|---|---|---|---|---|---|
| | 1 | 2 | 3 | 4 | 5 | 6 | 7 | 8 | 9 |
| Initial flowability [%] | 98.9 | 99.0 | 99.1 | 99.3 | 99.4 | 99.0 | 98.5 | 98.2 | 98.6 |
| Flowability after 20 minutes | 1.9 | 13.7 | 11.3 | 26.4 | 39.5 | 0.5 | 2.6 | 0.0 | 0.0 |

As shown by the above results, in accordance with the present invention, if stirring is performed at a mixing degree $M_{1\ min}$ of 0.1 or more in accordance with the present invention, a sol solution including a co-crystal which has high flowability without gelation, can be obtained. On the other hand, if stirring is performed at a mixing degree $M_{1\ min}$ of less than 0.1, the flowability will be lowered due to gelation.

INDUSTRIAL APPLICABILITY

According to the production method of the present invention, a co-crystal in a sol state can be stably obtained. Since the co-crystal sol obtained by the production method of the present invention is difficult to gelate, it is easy to handle and is suitable as a raw material for an agricultural and horticultural chemical composition. Therefore, the present invention is extremely useful from an industrial viewpoint.

EXPLANATION OF REFERENCES

1: stirring blade shaft
2: container
Circled number: sampling point

The invention claimed is:

1. A method for producing a co-crystal containing sol comprising:
   stirring a suspension comprising thiophanate-methyl, a triazole-based compound and a liquid medium at a mixing degree of 0.1 to 1.0, wherein
   the mixing degree is a ratio ($\sigma_r/\sigma_{1\ min}$) between a standard deviation $\sigma_r$ of thiophanate-methyl concentration in a suspension stirred to a completely mixed state and a standard deviation $\sigma_{1\ min}$ of thiophanate-methyl concentration in a suspension stirred for 1 min, the suspensions being obtained by adding a suspension agent containing 40% of thiophanate-methyl to a 1.2% xanthan gum gel solution.

2. The method according to claim 1, wherein the triazole-based compound is tebuconazole.

3. The method according to claim 1, wherein the suspension further comprises a surfactant.

4. The method according to claim 1, wherein the suspension further comprises an anti-foaming agent.

5. The method according to claim 1, wherein the temperature of the suspension during the stirring is 0 to 100° C.

6. An agricultural and horticultural chemical composition comprising the co-crystal containing sol obtained by the method defined in claim 1 and an auxiliary ingredient.

7. A method for producing an agricultural and horticultural chemical composition comprising:
   obtaining a co-crystal containing sol by the method defined in claim 1, followed by adding an auxiliary ingredient to the co-crystal containing sol.

* * * * *